US006558710B1

(12) United States Patent
Godfrey

(10) Patent No.: US 6,558,710 B1
(45) Date of Patent: May 6, 2003

(54) TOPICAL ZINC COMPOSITIONS AND METHODS OF USE

(76) Inventor: Helen Rebecca Godfrey, 1181 Mettler Rd., Huntingdon Valley, PA (US) 19006

( * ) Notice: Subject to any disclaimer, the term of this patent is extended or adjusted under 35 U.S.C. 154(b) by 0 days.

(21) Appl. No.: 09/332,508

(22) Filed: Jun. 14, 1999

(51) Int. Cl.[7] ...................... A61K 33/30; A61K 31/315; A61K 47/00
(52) U.S. Cl. ...................... 424/642; 424/405; 424/406; 424/409; 424/641; 424/DIG. 6; 514/494; 514/561; 514/772; 514/784; 514/788; 514/836; 514/922; 514/974
(58) Field of Search ................................ 424/641, 642, 424/405, 406, 409, 411, 443, 445, 446, 447, DIG. 6; 514/494, 772, 937, 788, 784, 922, 944, 969, 970, 974, 873, 561, 836

(56) References Cited

U.S. PATENT DOCUMENTS

| | | | |
|---|---|---|---|
| 4,339,432 A | 7/1982 | Ritchey et al. | 424/54 |
| 4,372,296 A | 2/1983 | Fahim | 601/2 |
| 4,407,818 A | 10/1983 | Lionelle et al. | 514/494 |
| 4,425,325 A | 1/1984 | Ritchey et al. | 424/54 |
| 4,465,666 A | 8/1984 | Lukas et al. | 424/78.05 |
| 4,565,693 A * | 1/1986 | Marschner | 424/67 |
| 4,684,528 A | 8/1987 | Godfrey | 426/74 |
| 4,711,780 A | 12/1987 | Fahim | 424/61 |
| 4,758,439 A | 7/1988 | Godfrey | 426/74 |
| 4,762,715 A | 8/1988 | Lukas et al. | 424/642 |
| 4,847,283 A | 7/1989 | Harendza-Harinxma | 514/415 |
| 4,937,234 A | 6/1990 | Fahim | 514/53 |
| 5,095,035 A | 3/1992 | Eby, III | 514/494 |
| 5,260,066 A | 11/1993 | Wood et al. | 424/447 |
| 5,409,905 A | 4/1995 | Eby, III | 514/23 |
| 5,482,053 A | 1/1996 | Kelly | 128/844 |
| 5,514,667 A | 5/1996 | Cullis-Hill | 514/54 |
| 5,545,673 A | 8/1996 | Kelly | 514/772.3 |
| 5,582,817 A | 12/1996 | Otsu | 424/59 |
| 5,599,551 A | 2/1997 | Kelly | 424/405 |
| 5,624,675 A | 4/1997 | Kelly | 424/405 |
| 5,696,169 A * | 12/1997 | Otsu et al. | 514/675 |
| 5,708,023 A | 1/1998 | Modak et al. | 514/494 |
| 5,759,559 A | 6/1998 | Fitzjarrell | 424/401 |
| 5,785,054 A | 7/1998 | Kelly | 128/842 |

FOREIGN PATENT DOCUMENTS

JP          57158724 A   *   9/1982

OTHER PUBLICATIONS

STN/CAS online,file CAPLUS, Acc. No. 1972:544383, Doc. No. 77:144383 (Gorzelany et al., Rocz. Chem. (1972), 46(5), 781–6), Abstract.*
Harrison's Principles of Internal Medicine, vol. 1 (13th Ed. 1994), pp. 481–483.*
Abstract—"Therapy of banal HSV lesions: molecular mechanisms of the antiviral activity of zinc sulfate" *Hautarzt:*, vol. 42, No. 7, pp. 439–445 (1991).

Agren, M. S., "Percutaneous Absorption of Zinc From Zinc Oxide Applied Topically to Intact Skin in Man", *Dermatologica*, vol. 180, No. 1, pp. 36–39 (1990)—Abstract.
Agren, M. S., Studies in "Zinc Wound Healing",*Acta Derm. Venereol. Suppl.*, vol. 154, pp. 1–36 (1990)—Abstract.
Amer, M. et al, "Serum Zinc in Acne Vulgaris" *International J. of Dermatology*, vol. 21, No. 8, pp. 481–484 (1982).
Arlette, J. P., "Zinc and the Skin" *Pediatrics Clinics of North America*, vol. 30, No. 3, pp. 583–595 (1983).
Brody, I., "Topical Treatment of Recurrent Herpes Simplex and Post–Herpetic Erythema Multiforme with Low Concentrations of Zinc Sulphate Solution" *British Journal of Dermatology*, vol. 104, pp. 191–194 (1981).
Bronson, D. M. et al, "Acrodermatitis enteropathic" *Journal of the American Academy of Dermatology*, vol. 9, No. 1, pp. 140–144 (1983).
Clinical Nutrition Case "Zinc Therapy of Depressed Cellular Immunity in Acrodermatitis Enteropathica" *Nutrition Reviews*, vol. 39, No. 4, pp. 168–170 (1981).
Crutchfield, C. E. et al, "The Highly Effective Use of Topical Zinc Pyrithione in the Treatment of Psoriasis: A Case Report", *Dermatol. Online J.*, vol. 3, No. 1, p. 3 (1997)—Abstract.
DeRoetth, A., "Treatment of Herpetic Keratitis", *American J. Ophthalmology*, 56, pp. 729–731 (1963).
Duchateau, J. et al, Stimulation of Specific Immune Response to Varicella Antigens in the Elderly with Varicella Vaccine *Postgraduate Medical Journal*, vol. 61, (Suppl. 4), pp. 147–150 (1985).
Eby, G. A. et al, "Use of Topical Zinc to Prevent Recurrent Herpes Simplex Infection: Review of Literature and Suggested Protocols" *Medical Hypotheses*, vol. 17, pp. 157–165 (1985).
Eriksson, G., "Local Treatment of Venous Leg Ulcers",*Acta Chir. Scand. Suppl.*, vol. 544 pp. 47–52 (1988)—Abstract.
Fahim, M. S. et al, New treatment for Herpes Simplex Virus Type 2 [Ultrasound and Zinc, Urea and Tannic Acid Ointment] Part II: Female Patients *Journal of Medicine*, vol. 11, Nos. 2 and 3, pp. 143–167 (1980).
Falanga, V. et al "Zinc Chloride Paste for the Debridement of Chronic Leg Ulcers" *J. Dermatol. Surg. Oncol.*, vol. 16, No. 7, pp. 658–661 (1990).
Fosmire, G. J. "Zinc toxicity" *Am. J. Clin. Nutr.*, vol. 51, pp. 225–227 (1990).
Finnerty, E. "Topical Zinc in the Treatment of Herpes Simplex" *Cutis*, 37(2), pp. 130–131 (1986).

(List continued on next page.)

Primary Examiner—Jose G. Dees
Assistant Examiner—Frank Choi
(74) *Attorney, Agent, or Firm*—Breiner & Breiner, L.L.C.

(57) ABSTRACT

Compositions including zinc compounds and select amino acids in a carrier base, and methods of skin treatment with such compositions, are described. The compositions are useful for healing skin and minimizing the irritation incurred from contact with the zinc compound without loss of zinc availability during absorption into the integument.

2 Claims, No Drawings

OTHER PUBLICATIONS

Godfrey, J. C. et al. "Zinc for Treating the Common Cold: Review of All Clinical Trials Since 1984" *Alternative Therapies*, vol. 2, No. 6, pp. 63–72 (1996).

Greaves M. W. et al, "Double–Blind Trial of Zinc Sulphate in the Treatment of Chronic Venous Leg Ulceration" *Br. J. Derm.* vol. 87, pp. 632–634 (1972).

Greaves, M. W. et al, "Effects of Long–Continued Ingestion of Zinc Sulphate in Patients with Venous Leg Ulceration" *The Lancet*, pp. 889–891 (1970).

Hallmans, G. et al, "The Effect of Zinc Tape Upon Wound Healing. A Biochemical, Histochemical and Histological Study In Rats", *Scand. J. Plast. Reconstr. Surg.*, vol. 13, No. 2, pp. 251–259 (1979)—Abstract.

Hansson, C. "Optimal Treatment of Venous (Stasis) Ulcers in Elderly Patients", *Drugs Aging*, vol. 5, No. 5, pp. 323–334 (1994)—Abstract.

Harper, Scott D. et al, "Clinical Efficacy of a Dentrifrice and Oral Rinse Containing Sanguinaria Extract and Zinc Chloride During 6 Months of Use", *J. Periodontol.*, vol. 61, No. 6, pp. 352–358 (1990).

Jannes, M. et al, "Protection by Zinc Against UVA– and UVB– Induced Cellular and Genomic Damage In Vivo and In Vitro", *Biol. Trace Elem. Res.*, vol. 53, Nos. 1–3, pp. 19–25 (1996)—Abstract.

Kümel, G. et al, "The Mechanism of the Antiherpetic Activity of Zinc Sulphate" *Journal of General Virology*, vol. 71, pp. 2989–2997 (1990).

Lansdown, A. B. G., "Interspecies Variations In Response To Topical Applications Of Selected Zinc Compounds" *Food and Chemical Toxicology* 29(1), pp. 57–64 (1991).

Lee, A. R. et al, "Zinc Sulphadiazines: Novel Topical Antimicrobial Agents for Burns", *J. Pharm. Pharmacol.*, vol. 47, No. 6, pp. 503–509 (1995)—Abstract.

*Microdex Health Care Series*, "Zinc Salts", (1998) (34 pages).

Moran, D. M. et al, "Zinc Defiency Dermatitis Accompanying Parenteral Nutrition Supplemented with Trace Elements", *Clin. Pharm.*, vol. 1, No. 2, pp. 169–176 (1982)—Abstract.

Murakami, J. L. et al, "The Effects of Zinc Oxide and Diethyldithiocarbamate on the Mitotic Index of Epidermal Basal Cells of Mouse Skin", *Acta Med. Okayama*, vol. 48, No. 5, pp. 231–236 (1994)—Abstract.

Neldner, K. H. et al, "Zinc Therapy of Acrodermatitis Enteropathica" *The New England Journal of Medicine*, vol. 292, No. 17, pp. 879–881 (1975).

Note entitled "Early Clinical Results Show Topical Agent Effective vs. Genital Herpes", *Hospital Practice*, pp. 44, 48 and 53 (1979).

Piérard–Franchimont et al, A Double–Blind Controlled Evaluation of the Sebossuppressive Activity of Topical Erythromycin–Zinc Complex, *Eur. J. Clin. Pharmacol.*, vol. 49, Nos. 1–2, pp. 57–60 (1995).

Prasad, A. S. "Clinical, Biochemical, and Pharmacological Role of Zinc" *Ann. Rev. Pharmacol. Toxicol*, vol. 20, pp. 393–426 (1979).

Prasad, A. S. "Clinical and Biochemical Manifestations of Zinc Deficiency in Human Subjects" *Journal of the American College of Nutrition*, vol. 4, pp. 65–72 (1985).

Prasad, A. S. "Zinc in Human Nutrition" *CRC Press, Inc.* pages Preface, Table of Contents, 30–31, 67–69, 74–83 (1979).

Samman, S. et al, "The Effect of Zinc Supplements on Plasma Zinc and Copper Levels and the Reported Symptoms in Healthy Volunteers" *The Medical Journal of Australia*, vol. 146, pp. 246, 248–249 (1987).

Schmidt, A. et al "Malassezia furfur: A Fungus Belonging to the Physiological Skin Flora and Its Relevance in Skin Disorders" *Continuing Medical Education*, vol. 59, pp. 21–24 (1997).

Schmidt, A. et al "In Vitro Susceptibility of Malassezia Furfur" *Arzneimittelforschung*, vol. 46, No. 4, pp. 442–444 (1996)—Abstract.

Serjeant, G. R. et al "Oral Zinc sulphate in Sickle–Cell Ulcers" *The Lancet*, pp. 891–892 (1970).

Shehade S. et al "Effects of Oral Zinc in Erythropoietic Protoporphyria" *Arch Dermatol.*, vol. 125, pp. 1713–1714 (1989).

Silvetti, A. N. et al, "Treatment of Basal Cell Carcinoma of the Face with Dilute Zinc Chloride Solution", *Clinical Research*, p. 550A—Abstract. 24(4) (1976).

Strömberg, H. E. et al, "Topical Zinc Oxide Treatment Improves Arterial and Venous Leg Ulcers" *British Journal of Dermatology*, vol. 111, pp. 461–468 (1984).

Sugarman, B. et al, "Zinc and Chlamydia Trachomatis", *Proc. Soc. Exp. Biol. Med.*, vol. 179, No. 3, pp. 382–387 (1985)—Abstract.

Tarnow, P. et al, "Topical Zinc Oxide Treatment Increases Endogenous Gene Expression of Insulin–Like Growth Factor–1 in Granulation Tissue from Porcine Wounds" *Scand. J. Plast. Reconstr. Hand Surg.*, vol. 28, pp. 255–259 (1994).

Wahba, A. "Topical Application of Zinc–Solutions: A New Treatment for Herpes Simplex Infections of the Skin?" *Acta Dermatovener (Stockholm)*, vol. 60, pp. 175–177 (1980).

* cited by examiner

TOPICAL ZINC COMPOSITIONS AND METHODS OF USE

FIELD OF INVENTION

The present invention relates to zinc-containing compositions and methods for topical use of such compositions to treat cutaneous wounds, irritations, lesions, abrasions or the like. More particularly, the invention relates to zinc-containing compositions containing an amino acid to minimize external irritation from the zinc when applied to the skin without diminishing the amount of free zinc available for absorption.

BACKGROUND OF THE INVENTION

The value of zinc in tissue growth and repair is well documented. Zinc is essential for the function of at least 70 enzymes and is involved in a variety of metabolic processes. Zinc is a limiting factor in the formation of RNA and DNA. Zinc is also a limiting factor in zinc-dependent enzymes such as RNA and DNA polymerases, deoxythymidine kinase, and reverse transcriptase, which are responsible for the regulation of RNA and DNA metabolism. Diminished zinc availability slows protein synthesis, thereby slowing the replication of cells and inhibiting tissue repair. Approximately half of the total body zinc content of 2–3 gm (based on an average 70 kg adult) is found in ossified tissues and is, therefore, not readily available for metabolic processes. Although the skin boasts a higher zinc concentration than most tissues (10 micrograms/g of tissue), this is quickly depleted during the regeneration process. It has been shown experimentally that the activity of deoxythymidine kinase in rapidly regenerating connective tissue decreases as early as six days after animals are placed on a zinc-deficient diet, demonstrating that an external supply of zinc for use in tissue repair is essential. In fact, zinc supplementation has been shown to markedly improve wound healing in zinc-deficient individuals, while topical zinc improves wound healing in zinc-deficient and in normal individuals.

Zinc salts are known to inhibit bacterial and viral growth. Ophthalmic preparations of zinc sulfate to treat herpetic keratitis have been recommended since 1943. Oral preparations of zinc citrate used to treat gingivitis and periodontitis have been shown to reduce plaque formation and inhibit bacterial growth. Oral preparations of several zinc salts have been shown to reduce the symptoms and duration of the common cold caused by rhinovirus, but they are unpalatable and cause mouth irritation and nausea. Until the development of a palatable and less irritating zinc salt-with-amino-acid formulation, patients often refused to continue treatment with the oral preparations containing zinc salts.

Successful topical treatment of skin infections and lesions with zinc salts is well documented. Topical zinc pyrithione is an effective anti-fungal, effective in treating *Malassezia furfur*, the causative agent in several skin disorders including pityriasis versicolor. Topical zinc pyrithione has also been used to treat psoriasis and dandruff by inhibiting the over-proliferation of cells characterized by these conditions. Application of a zinc chloride solution before and after UV exposure in hairless mice reduced the number of sunburn cells in the epidermis and was reported in 1976 as a successful topical treatment of basal cell carcinoma in a human patient. Erythromycinzinc lotion is sebosuppressive and potentially beneficial to the acneic patient.

Herpes of the lips occurs in 50% of the population, while genital herpes is now one of the most common venereal diseases. Zinc salts irreversibly inhibit herpes virus replication in vitro and are effective in treating herpes infections in vivo. Zinc ions irreversibly inhibit herpes simplex virus (HSV) glycoprotein functions by accumulating in the sulfhydryl groups of glycoprotein B in the viral membrane, blocking synthesis of DNA. In the closely related rhinovirus, it is theorized that free zinc ions also sequester in the membrane, inhibiting viral binding with ICAM receptor sites in mucous membranes. Other closely related viruses may similarly be affected by zinc ions. U.S. Pat. No. 5,545,673 cites in vitro evidence that HIV infectivity was reduced or completely eliminated when concentrated viral stocks were incubated with 1–1.5% zinc acetate for 2 hours. HSV has significant homology to varicella-zoster virus. Eruptions of herpes zoster are thought to be more frequent in the elderly not because of immune dysfunction, but because of slowed mobilization of the immune system. It follows that prompt treatment with a zinc salt would be extremely beneficial as it would markedly decrease viral load and painful lesions independent of immune system activation.

Zinc salt solutions applied to herpetic lesions decrease viral load and markedly improve healing rates, relieving the symptoms of herpes as healing occurs. Long-term topical application of zinc salt solutions appears to greatly reduce or eliminate recurrences of genital herpetic lesions as well as prevent post-herpetic erythema multiform. It has been postulated that the delivery of a high concentration (compared to natural tissue and body fluid levels of ionic zinc) of the virucidal agent to the infection site may prevent retrograde spread of virus along involved ganglia.

Zinc oxide has been shown in numerous studies to accelerate the healing of both chronic and acute wounds. This effect may be in part due to stimulation of epidermal basal cells, noted in mice, and in part due to increased insulin-like growth factor-1 and mRNA (messenger RNA), noted in granulation tissue of full-thickness wounds in domestic pigs. Zinc paste bandages containing inorganic zinc compounds, e.g., zinc sulfate and zinc oxide, have long been a standard treatment of venous stasis ulcers. Zinc chloride paste has been shown effective in debridement and formation of granulation tissue on chronic leg ulcers. Zinc oxide has been shown to promote cleansing and re-epithelialization of leg ulcers and to reduce infections and deterioration of ulcers.

Unfortunately, topical application of some zinc solutions can cause painful or irritating side effects if not used in very low concentrations. Zinc sulfate solutions of 0.2–1% can cause severe irritation, unpleasant dryness and stimulate the emetic reflex when applied circumorally.

Reports of dermal irritancy in animal dermal abrasion models examining wound healing show the following: 1% aqueous zinc chloride is severely irritant; 20% aqueous zinc acetate is slightly less irritant; 20% suspension zinc oxide, 1% aqueous zinc sulfate, and 20% suspension zinc pyrithione, are not overtly irritant. The less irritant zinc salts, such as zinc oxide (which is only slightly soluble in water), were only marginally effective in stimulating epidermal healing in comparison to the more irritating and more water-soluble zinc salts.

Further, it is interesting to note that in other studies the zinc solutions, particularly of zinc sulfate, do not maintain constant local concentration levels when applied to the skin as does zinc oxide. The zinc in these studies is not slowly solubilized to provide a constant level for absorption, being already in frank solution. This indicates that a zinc preparation that provides a higher concentration of solubilized zinc in a minimally irritating formulation allowing controlled absorption would be of great clinical value.

Compositions for treating various skin irritations are also known including zinc and another material or materials. Such are described, for example, in the following U.S. Patents:

U.S. Pat. No. 4,937,234 describes a pharmaceutically acceptable composition providing minerals(s) (e.g. Zn) in a bioavailable form by the inclusion of certain amino acids (see col. 2, lines 56–59), with the molar amount of an acidic mineral salt (e.g., zinc gluconate) to an amino acid (e.g., lysine) being from about 0.05M:1.0M to about 1.0M:0.05M and neutralized to a pH of 6–8. Zinc oxide is mentioned only as not being water insoluble. In Example 13, zinc oxide is solubilized in water by the addition of ascorbic-acid. Various skin irritations can be healed.

U.S. Pat. No. 4,711,780 describes a composition to treat surface epithelium to promote epithelial regeneration. The composition includes a mixture of a zinc salt, vitamin C, and a sulfur amino acid. Zinc oxide is not disclosed. The composition is stated to be useful in treating a wide variety of conditions, including of the skin, such as burns, cuts, fever blisters, poison ivy, chigger bites, diaper rash, genital herpes blisters, and sunburn. Depending on the locus of treatment, the composition will take different forms as appropriate, such as water, oil or gel vehicle; spray, or powder or medicated bandage.

U.S. Pat. No. 5,582,817 describes a composition for treating various skin diseases, see col. 6, lines 48–58. The composition includes a zinc salt, a zinc complex, or a salt of a zinc complex. The complex or salt thereof may be based on a zinc compound and an amino acid. Zinc oxide is mentioned and used only as a "relatively insoluble metal salt". The co-use of a solubilizing agent is not disclosed. The composition is stated to have unexpected action in inducing metallothionen and suppressing the production of sunburn cells by UV rays.

U.S. Pat. No. 5,708,023 describes a composition for application to a surface (such as skin) including an irritant-inactivating agent and a substance which prevents the irritant-inactivating agent from binding to the surface. Pharmaceutically acceptable cationic substances may also be used to block.binding sites, e.g., cations from relatively soluble zinc and zinc salts (e.g., zinc gluconate, zinc acetate and zinc sulfate). Examples of other pharmaceutically acceptable cationic substances disclosed are quaternary ammonium compounds which are then further defined as including amino acids. This further characterization, however, of quaternary ammonium compounds is in error. While quaternary ammonium compounds have four (4) groups (none of which is hydrogen) attached to one (1) nitrogen atom, which then possesses a positive(+) charge of 1, all 21 natural and biologically important amino acids have the structure R—CH(NH$_2$)—COOH. Clearly amino acids do not satisfy the described cationic substance. Examples of irritants suitable for treatment include HIV and the hepatitis virus.

U.S. Pat. No. 5,260,066 describes a cryogel (a hydrogel containing PVA) bandage containing a therapeutic agent such as inorganic and organic zinc salts as antimicrobials, and amino acids such as glycine. Zinc oxide is not disclosed.

Many existing topical formulations are inadequate because they produce such local irritation that they are not easily tolerated. Others also frequently lack a sufficient effective concentration of zinc ion due to the low solubility of zinc oxide in the absence of suitable solubilizing agents. Further, existing formulations have unpalatable tastes, making circumoral application impractical.

It would be highly desirable to have a topical zinc formulation and method of use that addresses the deficiencies in existing treatments.

OBJECTS AND BRIEF DESCRIPTION OF THE INVENTION

A primary object of the present invention is to provide a topical zinc composition for the management and healing of cutaneous wounds, irritations, abrasions and the like, including herpes-type lesions.

Another object of the invention is to provide a topical zinc composition that supplies a high effective concentration of available zinc and minimizes skin irritation.

Another object of the invention is to provide a topical zinc composition containing a select amino acid.

Another object of the invention is to provide a method of treating skin with a topical zinc composition containing a select amino acid.

The composition of the present invention includes (1) a pharmaceutically acceptable zinc compound, preferably zinc oxide or a divalent zinc complex, (2) a select amino acid, preferably glycine, and (3) a pharmaceutically acceptable carrier base, such as a solid.or semi-solid carrier base. The zinc compound is present in the carrier base together with a large excess of the amino acid (2 to 20 molar equivalents to the zinc) to provide a composition with high zinc ion availability and minimal skin irritance when topically applied to the skin.

A composition of the invention is used by applying the composition to an affected area of skin surface, and spreading the composition so as to contact and coat the area. Application to an affected area can be repeated periodically as needed until sufficient healing is achieved. The composition can also be applied to an occlusive or non-occlusive bandage. When the bandage is positioned on the skin, the composition contacts the skin to heal the affected area.

DETAILED DESCRIPTION OF PRESENTLY PREFERRED EMBODIMENTS OF THE INVENTION

According to the present invention, it has been found that compositions containing a zinc compound; an appropriate carrier base, for example a cream, balm, lotion, water-bearing ointment or the like; and certain amino acids, in which the molecular ratio of amino acid to zinc is in the range of 2:1 to 20:1, causes minimal irritation while providing sufficient free zinc ions for local absorption into the integument and zinc availability for viral inhibition and healing. The composition contains from about 1 mg to about 20 mg of zinc for each gram of the composition.

Zinc compounds which can be used in combination with certain amino acids can be in any of the forms commonly used such as the sulfate, chloride, acetate, gluconate, ascorbate, citrate, aspartate, picolinate, orotate and transferrin salts, as well as zinc oxide and complexes of divalent zinc with an amino acid. It has been found that zinc oxide solubilized with glycine is particularly preferred.

Amino acids useful for the purpose of this invention are glycine, L-lysine, and D,L-lysine.

Suitable useful complexes are formed by reacting zinc oxide with monocarboxylic acids of the named amino acids and have the composition Zn(Amino Acid)$_2$. These complexes are water-soluble, particularly in the presence of excess amino acid, release substantially all of the zinc as Zn$^{2+}$ ion into aqueous solution, are minimally irritating because the amino acid modifies the irritant effect of the zinc, and have very good flavors, taste being an important consideration as the invention can be applied circumorally. However, amino acids, such as aspartic and glutamic acids, are not useful for forming the above complexes. These amino acids are dicarboxylic. Preferred complexes of divalent zinc with monocarboxylic amino acid are a zinc glycine complex having a formula Zn(C$_2$H$_4$NO$_2$)$_2$·nH$_2$O in which n has a value of 1, 1½, or 2, combined with from 0.3 to 5.4 parts by weight of anhydrous glycine; and a zinc D,L-lysine complex having a formula Zn(C$_6$H$_{13}$N$_2$O$_2$)$_2$·4H$_2$O combined with from 0.9 to 3.5 parts by weight of anhydrous glycine.

Preferred complexes of divalent zinc with monocarboxylic amino acid are a zinc glycine complex having a formula Zn(C$_2$H$_4$NO$_2$)$_2$.nH$_2$O in which n has a value of 1, 1½, or 2, combined with from 0.3 to 5.4 parts by weight of anhydrous glycine; and a zinc D,L-lysine complex having a formula Zn(C$_6$H$_{13}$N$_2$O$_2$)$_2$.4H$_2$O combined with from 0.35 to 3.5 parts by weight of anhydrous glycine.

Appropriate carrier base compounds can contain components selected from a broad range of pharmaceutically acceptable materials known in the art of preparation of topical solid or semi-solid formulations, such as creams, moisturizing creams, lotions, emollients, balms and the like. Such a base formulation can include, but is not limited to purified water, sunflower oil, stearic acid, cocoa butter, monoglyceryl stearate, stearic triglyceride, stearyl alcohol, aloe barbadensis gel, jojoba oil, αtocopheryl acetate (Vitamin E), carrot extract, jasmine extract, chamomile extract, calendula extract, red clover blossom extract, methyl paraben, propyl paraben, caramel, retinyl palmitate and fragrance oil.

It is important that no component of such base formulation possesses the potential for strong chelation of ionic zinc, for the presence of such compound will inactivate the zinc ions which provide the desired physiological benefit of availability for enzyme use to enhance tissue proliferation and healing as well as antiviral activity. The chemical principles which govern the chelation of metal ions by organic compounds are well known such that one skilled in the art can determine by visual inspection of a written chemical structure whether or not a given chemical compound has the potential for strong chelation of ionic zinc. (taking into account pH changes which can be caused by the base). It is well known, for example, that such varied structures as those represented by citric acid, tartaric acid, 8-hydroxyquinoline, orthophenanthroline, and ethylenediaminetetraacetic acid (EDTA), are structurally and electronically configured so as to form very tight, i.e. highly stable, chelated complexes with zinc ion. Thus, any structures which are chemical analogs of the aforementioned strong chelating compounds, or any others of of such compounds, are to be avoided in formulating the carrier base.

The compositions of the invention are also suitable for application to the skin by means of an occlusive or non-occlusive bandage or dressing. The compositions of the invention can be carried on a bandage in a conventional manner. When the bandage is positioned on the skin over an area to be treated, the composition comes into contact with the skin and acts on the skin in the same manner as described above in relation to directly applied compositions.

Thus, zinc-containing compositions prepared according to the present invention, include pharmaceutically acceptable zinc oxide and a select amino acid. The compositions possess a very pleasant flavor, modify the irritant effect of zinc, and release ionic zinc into a semi-aqueous solution and/or suspension at concentrations that are calculated to be on the order of one thousand times the normal blood level of zinc. The very high concentration gradient between available ionic zinc at the epithelial surface and the blood and tissue fluid zinc concentrations coupled with the effect of the components of the creams, balms, ointments, etc. (with respect to facilitation of the penetration of the zinc ions through the epithelial layer) provides the strong anti-viral and wound-healing enhancement properties of zinc to be made available where they are needed in order to effectively treat the skin.

The following examples illustrate compositions of the invention and methods for preparing topical application formulations.

EXAMPLE 1

Zinc-Containing Moisturizing Cream with Vitamin E and Cocoa Butter

A moisturizing cream base was prepared containing the following ingredients: purified water, sunflower oil, stearic acid, cocoa butter, monoglyceryl stearate, stearic triglyceride, stearyl alcohol, aloe barbadensis gel, jojoba oil, α-tocopheryl acetate (Vitamin E), carrot extract, jasmine extract, chamomile extract, calendula extract, red clover blossom extract, methyl paraben, propyl paraben, caramel, retinyl palmitate and fragrance oil. The base ingredients were utilized in conventional amounts in view of the purpose to provide a moisturizing cream. A mixture of 0.440 g zinc oxide and 4.05 g anhydrous glycine was dissolved in 6.8 g purified water by heating in a Pyrex beaker to 160° F. in a 750 watt microwave oven. The clear, hot solution was added to 115 g of the cream base and was blended thoroughly to a smooth opaque cream which contained 0.279% Zn$^{2+}$. The product had acceptable consistency, flavor and astringency without causing irritating effects upon application.

In a test of efficacy against Herpes Simplex Virus (HSV) Type 1, a labial (lower oral lip) developing cold sore in an individual known to have recurrent HSV at the specific lower lip site was treated within 2 hours of the onset of typical prodromal symptoms (i.e. sensitivity, erythema, mild edema, tingling) by manual application of approximately 50 mg of the cream to the developing lesion. Relief of symptoms occurred within minutes. Cream application was repeated every 3–4 hours for 16 hours. Treatment was truncated because symptoms were eradicated at that time. A small, painless open lesion subsequently developed at 24 hours with rapid resolution.

EXAMPLE 2

Aloe Vera Ointment Containing Zinc

A 35.5 g aloe vera ointment base (including water, glyceryl stearate, PEG-100 stearate, glycerine, aloe vera gel, magnesium aluminum silicate, PEG-150 distearate, stearyl alcohol, quaternium 15, fragrance oil, diazolidinyl urea, and methyl paraben) was combined with 0.187 g zinc oxide and 1.73 g glycine dissolved in 2.9 g purified water at 160° F. in a small Pyrex bowl. The stirred mass was warmed to 110–115° F., at which point the mixture could be evenly blended to a smooth, translucent ointment by rubber spatula. The zinc content of the product was 0.37%. The product had

EXAMPLE 3

Vitamin E Ointment with Zinc

A 45.4 g Vitamin E ointment base including petrolatum, isopropyl myristate, α-tocopheryl acetate (Vitamin E acetate), candelilla wax, cetyl alcohol, retinyl palmitate (Vitamin A palmitate), lecithin, and natural fragrance was combined with 0.180 g zinc oxide and 1.67 g glycine (dissolved in 2.8 g purified water at 160° F.) in a small Pyrex bowl and blended together by vigorous stirring with a rubber spatula. The product was a smooth, pale, yellow, and slightly-translucent ointment. The zinc content of the product was 0.29%. The product had acceptable consistency, flavor and astringency without causing irritating effects upon application.

EXAMPLE 4

Aloe Vera and Vitamin E Balm with Zinc 60 g of an aloe vera extract and tocopherol (Vitamin E) base including lilly white gel, paraffin, beeswax, panthenol, SHEA butter, squalene, olive oil, copaiba oil, kukui nut oil, babassu oil, octyl methoxycinnamate (sunscreen), safflower oil, soy oil and flavoring was combined with 0.243 g zinc oxide and 2.24 g glycine (dissolved in 3.76 g purified water at 160° F.) in a small Pyrex bowl and blended together by vigorous stirring with a rubber spatula. The product was a pale, smooth, slightly translucent balm. The zinc content of the product was 0.29%. The product had acceptable consistency, flavor and astringency without causing irritating effects upon application.

As will be apparent to one skilled in the art, various modifications can be made within the scope of the preceding description. Such modifications being within the ability of one skilled in the art form a part of the present invention and are embraced by the appended claims.

It is claimed:

1. A composition for topical skin application comprising:
   a pharmaceutically acceptable carrier base including one or more topical solid or semi-solid materials;
   zinc oxide and optionally at least one additional zinc compound; and
   at least one amino acid which is a monocarboxylic amino acid capable of forming a complex with said zinc oxide;
   wherein said at least one amino acid is present in an amount corresponding to from approximately 2 to 20 molar equivalents relative to zinc in the composition, said composition contains from about 1 mg to about 20 mg zinc for each gram of said composition, wherein zinc of the zinc oxide and said at least one additional zinc compound which is optionally present has a modified irritant effect so as to cause minimal skin irritation, wherein said composition provides free zinc ions for local absorption and zinc availability on an order of one thousand times a normal blood level of zinc, and wherein said zinc oxide serves to form a complex of divalent zinc with said monocarboxylic amino acid and said complex is a zinc glycine complex having a formula $Zn(C_2H_4NO_2)_2 \cdot nH_2O$ in which n has a value of 1, 1½, or 2, combined with from 0.3 to 5.4 parts by weight of anhydrous glycine.

2. A composition for topical skin application comprising:
   a pharmaceutically acceptable carrier base including one or more topical solid or semi-solid materials;
   zinc oxide and optionally at least one additional zinc compound; and
   at least one amino acid which is a monocarboxylic amino acid capable of forming a complex with said zinc oxide;
   wherein said at least one amino acid is present in an amount corresponding to from approximately 2 to 20 molar equivalents relative to zinc in the composition, said composition contains from about 1 mg to about 20 mg zinc for each gram of said composition, wherein zinc of the zinc oxide and said at least one additional zinc compound which is optionally present has a modified irritant effect so as to cause minimal skin irritation, wherein said composition provides free zinc ions for local absorption and zinc availability on an order of one thousand times a normal blood level of zinc, and wherein said zinc oxide serves to form a complex of divalent zinc with said monocarboxylic amino acid and said complex is a zinc D,L-lysine complex having a formula $Zn(C_6H_{13}N_2O_2)_2 \cdot 4H_2O$ combined with from 0.9 to 3.5 parts by weight of anhydrous glycine.

* * * * *